United States Patent [19]
Wales et al.

[11] Patent Number: 5,702,408
[45] Date of Patent: Dec. 30, 1997

[54] ARTICULATING SURGICAL INSTRUMENT

[75] Inventors: Kenneth S. Wales, Mason; Joseph F. Paraschac, Dayton; David Stefanchik, Mason, all of Ohio

[73] Assignee: Ethicon Endo-Surgery, Inc., Cincinnati, Ohio

[21] Appl. No.: 684,282

[22] Filed: Jul. 17, 1996

[51] Int. Cl.⁶ .................................................. A61B 17/10
[52] U.S. Cl. ........................ 606/139; 606/142; 606/144; 606/205
[58] Field of Search ...................... 606/139, 142–144, 606/148, 205, 208; 81/342, 345–348, 350, 351; 227/175.1, 175.2, 181.1, 182.1

[56] References Cited

U.S. PATENT DOCUMENTS

| | | | |
|---|---|---|---|
| 4,728,020 | 3/1988 | Green et al. ........................ | 227/19 |
| 4,869,414 | 9/1989 | Green et al. ........................ | 227/19 |
| 5,312,023 | 5/1994 | Green et al. ........................ | 227/175 |
| 5,326,013 | 7/1994 | Green et al. ........................ | 227/176 |
| 5,330,502 | 7/1994 | Hassler et al. ...................... | 606/205 |
| 5,374,277 | 12/1994 | Hassler ............................... | 606/207 |
| 5,381,943 | 1/1995 | Allen et al. ......................... | 227/177 |
| 5,383,888 | 1/1995 | Zvenyatsky et al. ................ | 606/206 |
| 5,403,342 | 4/1995 | Tovey et al. ........................ | 606/205 |
| 5,405,344 | 4/1995 | Williamson et al. ................ | 606/1 |
| 5,409,498 | 4/1995 | Braddock et al. ................... | 606/143 |
| 5,411,519 | 5/1995 | Tovey et al. ........................ | 606/207 |
| 5,417,203 | 5/1995 | Tovey et al. ........................ | 128/4 |
| 5,456,684 | 10/1995 | Schmidt et al. ..................... | 606/41 |
| 5,474,571 | 12/1995 | Lang .................................... | 606/205 |
| 5,497,933 | 3/1996 | DeFonzo et al. .................... | 227/175.1 |

*Primary Examiner*—Michael Buiz
*Assistant Examiner*—Tina T. D. Pham
*Attorney, Agent, or Firm*—Matthew S. Goodwin

[57] ABSTRACT

A four-bar linkage for an articulation assembly adapted for use with a surgical instrument is disclosed. The first link is in the form of an actuation lever which pivots transversely to the longitudinal axis of the instrument. The second and third links are operatively connected to the first link. The fourth link is in the form of an end effector for the instrument, and it is rotatably attached to the second and third links for movement transverse to the longitudinal axis. When the first link is pivotally rotated, a driver assembly causes the second and third links to move in tandem generally parallel to the longitudinal axis of the instrument in opposite directions. Consequently, the end effector rotates in the same direction as that of the actuation lever from an unarticulated position to an articulated position. The four-bar linkage is simple and efficient, and eliminates the need for a conventional central pivot for the articulation joint. By making the linkage the primary structural support of the end effector, clearance can be provided centrally between the second and third links to allow for the passage of additional linkages and members which are needed to actuate the end effector to carry out various surgical functions.

8 Claims, 9 Drawing Sheets

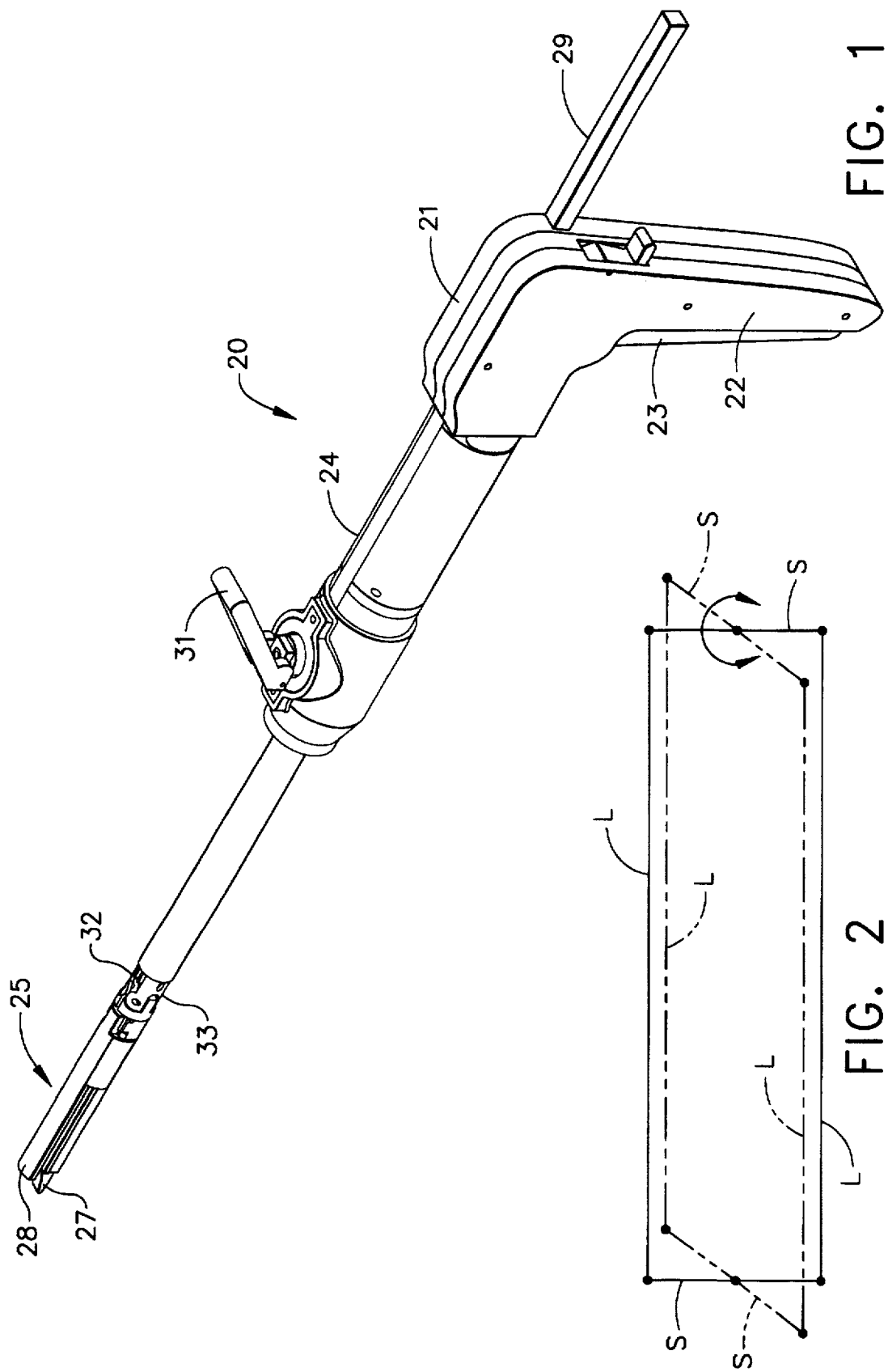

ARTICULATING SURGICAL INSTRUMENT

BACKGROUND OF THE INVENTION

This invention relates to a surgical instrument which facilitates precise placement of its "end effector" at the desired surgical site. More particularly, it relates to such an instrument where the end effector can be "articulated" or pivoted relative to the instrument shaft to facilitate desired positioning.

A surgical instrument routinely includes a frame, a shaft extending from the frame, and an end effector. The end effector carries the surgical implement which, when actuated, performs a desired surgical function. The frame typically includes a handle in the form of a pistol grip or scissors-type handle to actuate the end effector.

Often, it is necessary to adjust the positioning of the end effector of a surgical instrument to properly carry out the desired procedure. This often means that it is necessary to orient the end effector at an axis transverse to the long axis of the shaft of the instrument. The transverse movement of the end effector relative to the instrument shaft is conventionally referred to as "articulation". Descriptions of articulating surgical instruments are plentiful, and can be found, for example, in U.S. Pat. Nos. 4,728,020; 4,869,414; 5,312,023; 5,326,013; 5,330,502; 5,374,277; 5,381,943; 5,383,888; 5,403,342; 5,405,344; 5,409,498; 5,411,519; 5,417,203 and 5,456,684. Additionally, commonly assigned, co-pending U.S. application Ser. Nos. 259,322, filed Jun. 10, 1994; 359,107, filed Dec. 19, 1994; and 442,783, filed May 18, 1995 also describe articulating surgical instruments.

Although numerous surgical instruments have been described with alternative articulation mechanisms, these mechanisms are not without their problems. One major problem with most of these mechanisms is that the articulation linkage is not directly attached to the actuator in the frame of the instrument. Frequently, the actuator is attached to various linkages such as rods and cables which are in turn attached to some type of pivot joint adjacent the end effector. Unfortunately, the indirect association between the actuation mechanism in the frame of the instrument and the articulation joint adjacent the end effector causes significant inefficiencies which are undesirable. These inefficiencies translate into the need to generate high forces on the handle to effect articulation and an increased tendency to break the articulation joint when the end effector is subjected to high loads during tissue manipulation. If the articulation joint does not break, then it may undesirably deflect when loaded and therefore reduce the user's control over the precise positioning of the end effector.

Another problem with the articulation mechanisms of the prior art is that the central articulation joint, which is typically a pivot pin, occupies the central neutral axis of the instrument. While this may be convenient for the design of the articulation joint, it is problematical for the design of components and linkages in the shaft which must transmit forces from the frame to the end effector to carry out other surgical functions. For example, a surgical stapler often includes an end effector which clamps tissue between an anvil and a staple cartridge. When tissue is clamped, staples are fired from the cartridge into the clamped tissue. The clamping and firing mechanisms must be actuated from the frame. Therefore, the force transmission elements must be housed in the shaft and extend through the articulation joint into the end effector. When the articulation joint occupies the central neutral axis of the instrument, the other force transition members must be positioned around this joint. Unfortunately, the central axis is the optimum axis to deliver force, and therefore efficiencies are reduced.

Since there is room for improving conventional articulating surgical instruments, a surgical instrument which incorporates an alternative articulation mechanism is needed. Specifically, it would be desirable if an articulating surgical instrument were developed which did not incorporate the conventional central pivot pin for the articulation joint. It would also be beneficial if an articulation mechanism were described which is attached directly to the actuation mechanism in the frame of the instrument. In addition, an articulating surgical instrument is needed which exhibits little or no deflection on the end effector when it is in an articulated position and it is subjected to a high load. Finally, it would be desirable if such an instrument would incorporate an articulation mechanism which would allow for the critical room needed in the center of the shaft adjacent the end effector for the incorporation of additional linkages and members which are needed to actuate the end effector to carry out various surgical functions.

SUMMARY OF THE INVENTION

The invention is an articulation assembly adapted for use with a surgical instrument in which the instrument has a longitudinal axis. The articulation assembly comprises a four-bar linkage. The four-bar linkage includes four links.

The first link is in the form of an actuation lever. It is operatively connected to the instrument for movement transverse to the longitudinal axis of the instrument.

The second and third links are operatively connected to the first link for reciprocating movement by a driver assembly mounted to the instrument. The second and third links are generally parallel to each other, and parallel to the longitudinal axis of the instrument.

The fourth link is in the form of an end effector for the instrument. It is attached to the second and third links for movement transverse to the longitudinal axis of the instrument.

When the first link in the form of the actuation lever is pivotally rotated in a first direction from an unactuated position generally parallel to the longitudinal axis of the instrument to an actuated position, the following actions occur:

a) the driver assembly causes the second and third links to move in tandem generally parallel to the longitudinal axis of the instrument in opposite directions, b) the second and third links move inwardly towards each other from a spaced-apart position to an adjacent position, and c) the fourth link which is in the form of the end effector of the instrument rotates in said first direction from an unarticulated position to an articulated position.

The articulation assembly adapted for use with the surgical instrument of this invention uses a simple, efficient four-bar linkage to provide desired articulation of the end effector for precise positioning of the end effector at the surgical site within the body cavity. Significantly, a conventional central pivot pin for the articulation joint is unnecessary when the four-bar linkage of the articulation assembly is used. The second and third links are directly coupled to the end effector at the distal end and the actuation lever at the proximal end to efficiently articulate the end effector in direct response to pivotal movement of the actuator. In an articulated position, the end effector can withstand high loads to minimize deflection. Furthermore, the four-bar linkage can be provided to enable the passage of additional linkages and members centrally between the second and third links to actuate the end effector to carry out various surgical procedures.

The articulation assembly of this invention is particularly adapted for use with a surgical instrument. It may be used on surgical instruments for endoscopic and conventional open surgical procedures. However, it is particularly adapted for instruments which are used in endoscopic and other minimally invasive surgical procedures.

BRIEF DESCRIPTION OF THE DRAWINGS

FIG. 1 is an isometric view of an endoscopic linear stapler incorporating the preferred embodiment of an articulation assembly for articulating the end effector of the stapler.

FIG. 2 is a schematic plan view of the four bar linkage of the articulation assembly utilized in the stapler illustrated in FIG. 1. The unactuated position is shown in solid line. An articulated position is shown in phantom line.

DETAILED DESCRIPTION OF THE PREFERRED EMBODIMENTS

Figure 3:
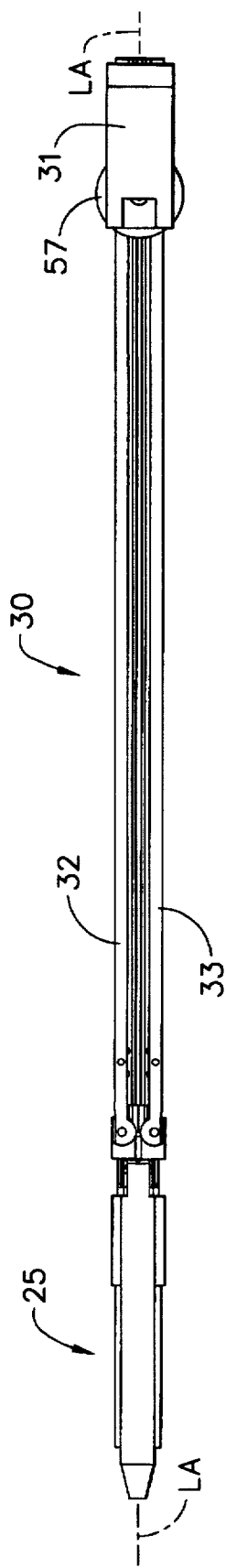
FIG. 3 is a plan view of the four bar linkage of the articulation assembly of the endoscopic linear stapler of FIG. 1.

Referring initially to FIG. 1, an endoscopic linear stapler 20 is shown. It has a frame 21 with a hand grip 22 for gripping and manipulating the instrument, and a closure trigger 23 coupled to the frame and adjacent the hand grip. Part of the frame is an elongated, cylindrical section 24. An end effector 25 for performing the desired surgical function is coupled to the distal end of the elongated links 32 and 33 (described in further detail below). In this case, the end effector is a surgical fastening assembly which carries a surgical cartridge 27 containing a plurality of staples therein (not shown) and an anvil 28 facing the cartridge for formation of the staples thereon when the firing trigger is actuated.

The stapler shown in FIG. 1 is shown in the closed position, where the closure trigger has been squeezed against the hand grip to close the anvil against the cartridge. Conventionally, endoscopic linear staplers have an anvil which is movable towards and away from the cartridge for initially inserting tissue therebetween and then clamping the inserted tissue. Once tissue is clamped, the firing trigger 29 is actuated to drive staples from the cartridge into the clamped tissue for formation against the anvil. Concurrently, with the driving of the staples into the clamped tissue, a knife blade (not shown) slides forwardly through slots in the cartridge and anvil to transect tissue between rows of stapled tissue. These endoscopic linear staplers, more commonly referred to as endoscopic linear cutters, are well known and described, for example, in U.S. Pat. No. 5,465,895.

The endoscopic linear cutter depicted in FIG. 1 is an articulating linear cutter. The articulation assembly of the cutter, described in more detail below, effects the remote articulation of the end effector to precisely position the end effector during minimally invasive surgery. Consequently, when the articulation lever 31 of the cutter is depressed and rotated, the end effector is caused to correspondingly rotate to provide the desired articulation, as will be described in connection with the description of the figures appearing hereinafter.

The articulation assembly for the articulating linear cutter depicted in FIG. 1 has a four bar linkage. Conceptually, a top view of the four bar linkage is illustrated in FIG. 2. Referring to the solid lines in FIG. 2, the four bar linkage includes a pair of parallel short links designated as "S" separated by a pair of parallel long links designated as "L". When the four bar linkage is actuated by rotational movement of a short link as illustrated with the directional arrow, the phantom lines in FIG. 2 illustrate the relative movement of the long links to cause an articulation of the opposite short link.

Figure 4:
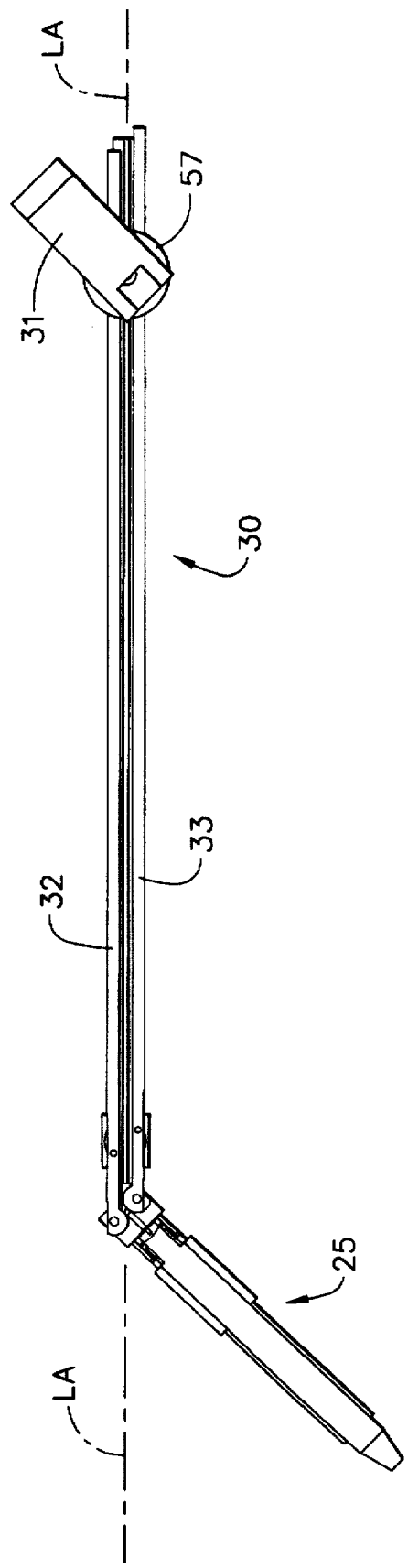
FIG. 4 is a plan view of the four bar linkage of the articulation assembly of FIG. 3 shown in an articulated position.

Referring to FIG. 1 in combination with FIGS. 3 and 4, a four bar linkage of an articulation assembly 30 of the articulating endoscopic cutter of FIG. 1 is shown. The first link 31 is in the form of an actuation lever (depicted nicely in FIG. 1). Second and third elongated links, 32 and 33, respectively, are coupled to the actuation lever at their proximal ends. The fourth link is the end effector 25 for the instrument (again depicted nicely in FIG. 1). It is coupled at its proximal end to the distal ends of the second and third links. As illustrated in FIG. 3, the four bar linkage is displayed in its unarticulated position in which the end effector is parallel to the longitudinal axis of the instrument (designated as "LA"). When the actuation lever is rotated from a position parallel to the longitudinal axis to a position transverse from the longitudinal axis in a first direction, it is noteworthy that, as illustrated specifically in FIG. 4, the end effector rotates from its position parallel to the longitudinal axis to an articulated position transverse to the longitudinal axis in the same the direction as that of the actuation lever. Rotation of the actuation lever causes the second and third links to reciprocate in opposite directions. In their unarticulated positions, the second and third links are spaced from and parallel to each other. In their articulated position illustrated in FIG. 4, the second and third links move parallel to each other in opposite directions, and additionally move inwardly relative to each other from their initial spaced apart position to an adjacent position.

Figure 5:
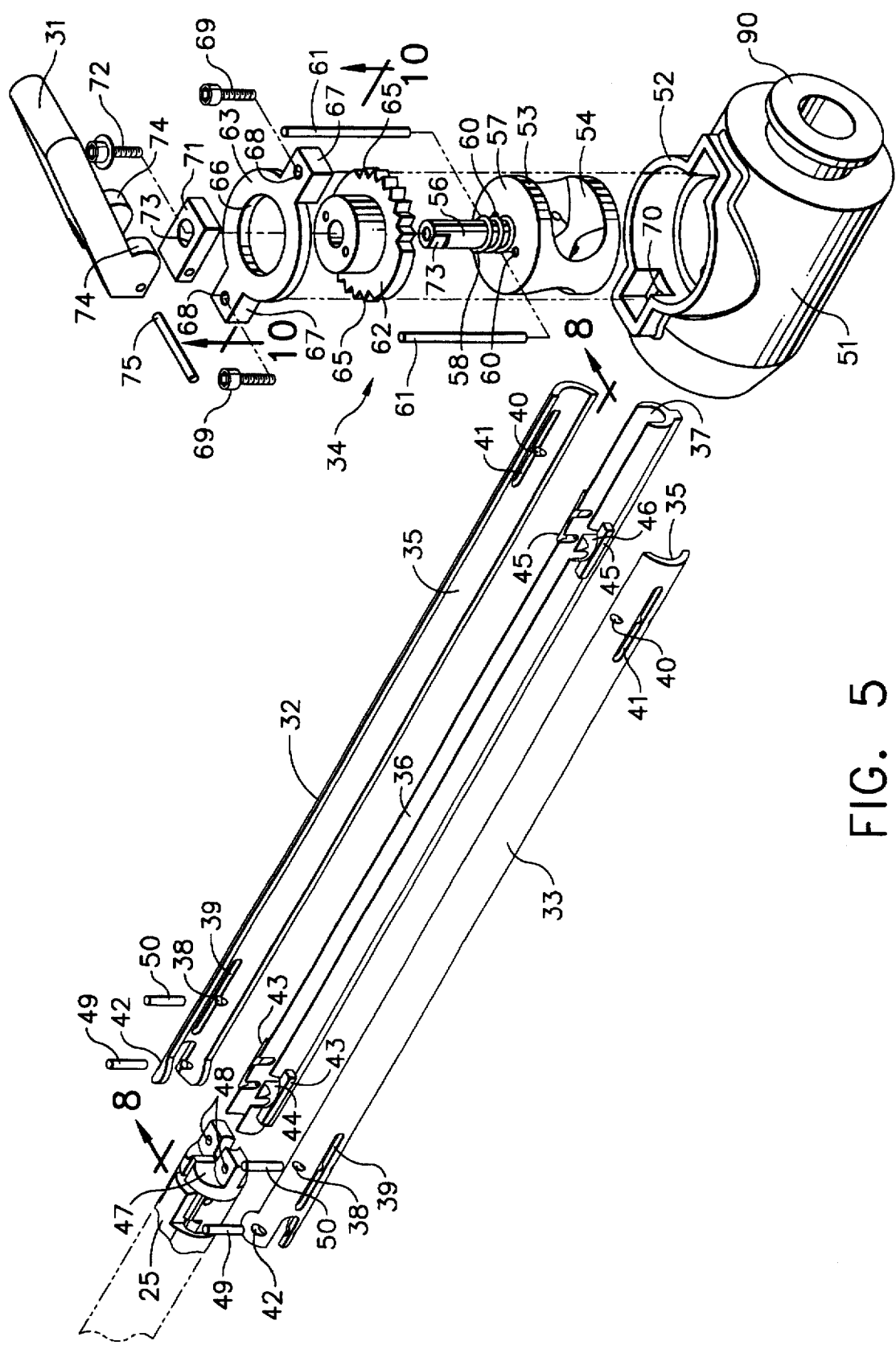
FIG. 5 is an exploded isometric view of the articulation assembly of the endoscopic linear stapler of FIG. 1, including the driver assembly for actuating the four bar linkage of the articulation assembly.

Referring now to FIG. 5 in combination with FIGS. 6-16, the details of the four bar linkage of the articulation assembly and the driver assembly 34 for causing reciprocating movement of the second and third links, 32 and 33, in response to rotational movement of the actuation lever 31 is illustrated. The second and third links are rigid elongated links. Each of these links has an arcuate concave surface 35, and the arcuate concave surfaces face each other. Separating the second and third links is an elongated, lateral support spider 36 which has a central channel 37 therethrough for enabling the passage of other elements and linkages through the assembly to the end effector 25 for carrying out various surgical functions.

Figure 8:
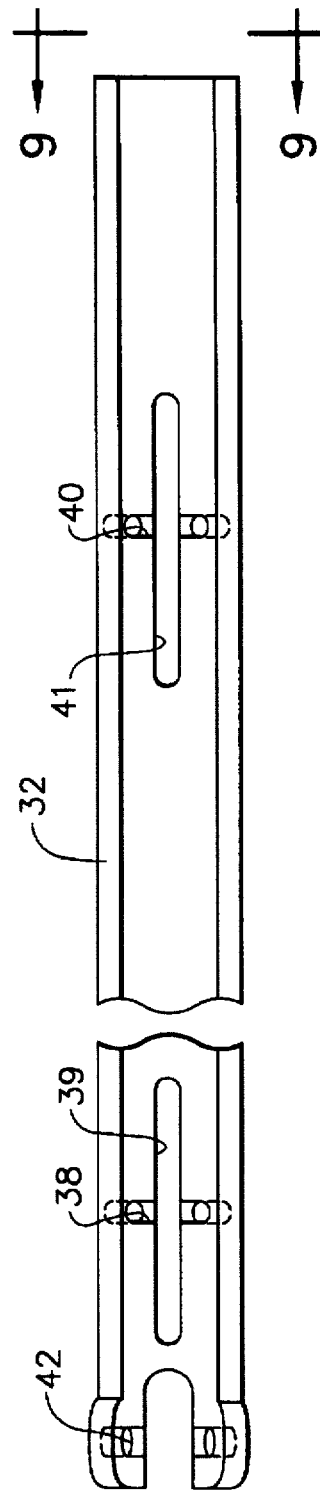
FIG. 8 is a foreshortened elevational view of the second link taken along line 8—8 of FIG. 5.
Figure 9:
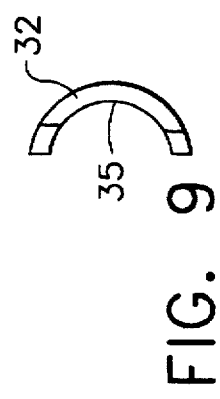
FIG. 9 is an end elevational view of the second link shown in FIG. 8.
Figure 10:
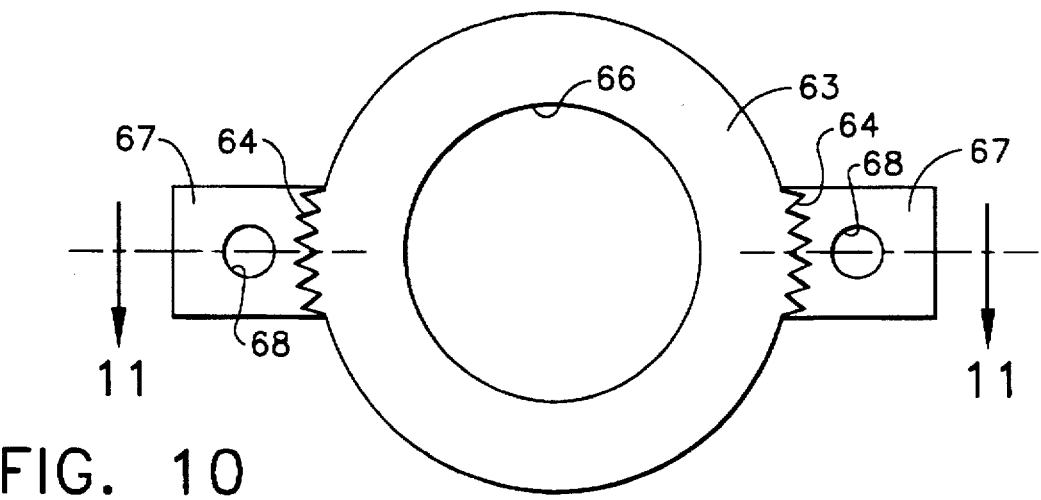
FIG. 10 is a bottom view of a locking plate for the driver assembly taken along line 10—10 of FIG. 5.
Figure 11:
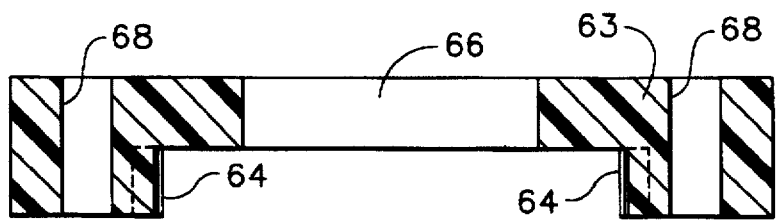
FIG. 11 is a section view of the locking plate taken along line 11—11 of FIG. 10.
Figure 12:
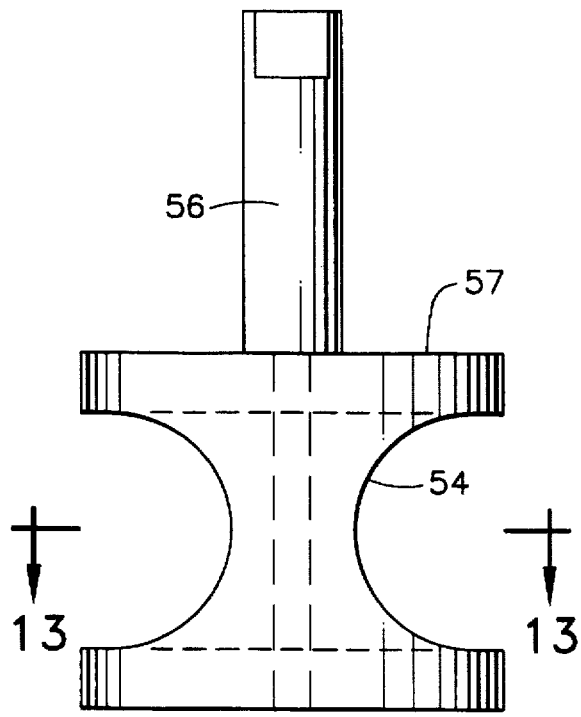
FIG. 12 is a side elevation view of a spool for the driver assembly shown in FIG. 5.
Figure 13:
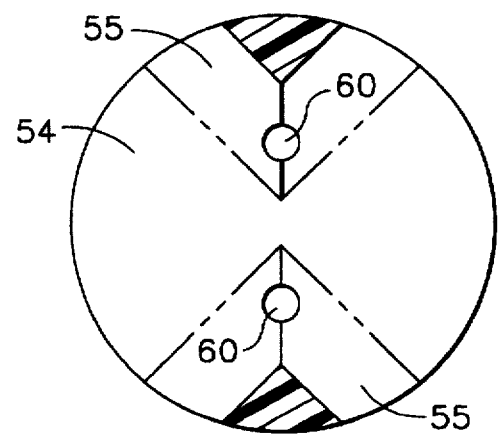
FIG. 13 is a section view of the spool taken along line 13—13 of FIG. 12.

In reviewing FIG. 5 in combination with FIGS. 8 and 9, each of the second and third links has a vertical front guide hole 38 and a front guide slot 39, and a vertical rear guide hole 40 and a rear guide slot 41. At the distal end of each of the second and third links, there is a distal vertical hole 42.

Figure 7:
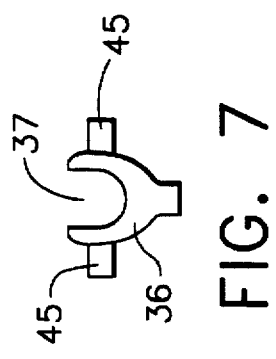
FIG. 7 is an end elevation view of the lateral support spider shown in FIG. 6.
Figure 6:
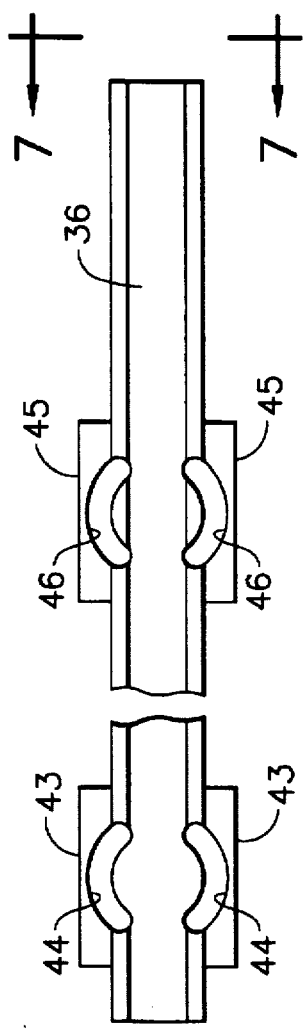
FIG. 6 is a foreshortened plan view of a lateral support spider providing support for the second and third links of the articulation assembly illustrated in FIG. 3.

In reviewing FIG. 5 in combination with FIGS. 6 and 7, the lateral support spider 36 has a pair of front guide tabs 43 and front arcuate slots 44, and a pair of rear guide tabs 45 and rear arcuate slots 46.

The fourth link in the form of the end effector has on its proximal end a pivot block 47. The pivot block has a pair of pivot holes 48 which during assembly are aligned with the distal vertical holes 42 of the second and third links, 32 and 33.

When the second and third links are assembled, and their distal ends are coupled to the end effector, the pair of front and rear guide tabs, 43 and 45, on the elongated, lateral support spider 36 are received within the front and rear guide slots, 44 and 46, respectively, of the second and third links. Therefore, the second and third links are free to reciprocate longitudinally relative to the spider. A pair of pivot block pins 49 are inserted through the distal vertical holes 42 of the second and third links and the pair of pivot holes 48 on the pivot block 47 attached to the end effector to rotatably couple the proximal end of the end effector to the distal end of the second and third links. A pair of short guide pins 50 are inserted into the vertical front guide holes 38 of the second and third links and through the pair of front arcuate slots 44 of the spider to provide guidance to the second and third links during reciprocating longitudinal movement.

The driver assembly 34 for effecting reciprocating movement of the second and third links in response to rotational movement of the actuation lever 31 will now be explained. The driver assembly has a nozzle body 51 with a mounting flange 90 to mount the driver assembly onto the endoscopic linear cutter. The nozzle body has a nozzle housing 52 extending from it. A spool 53 is inserted into and received within the nozzle housing. In reviewing FIG. 5 in combination with FIGS. 12 and 13, the spool has an obround hole 54 through it. The obround hole has flared clearances 55 to permit pivoting of the second and third links when assembled. The spool also has an upstanding shaft 56 extending from a spool base 57. A locking spring 58 is mounted on the upstanding shaft. Extending through the base of the spool are a pair of pin holes 60 on either side of the upstanding shaft. When the spool is received within the nozzle housing so that the obround hole thereof is in axial alignment with the nozzle body, the proximal ends of the second and third links, 32 and 33, and the lateral support spider 36, are inserted into and received within the nozzle body and through the obround hole of the spool. When properly inserted, a pair of long spool pins 61 are inserted downwardly through the pin holes 60 of the spool and into the rear guide holes 40 and rear arcuate slots 46 of the second and third links, and the spider, respectively. Accordingly, the proximal ends of the second and third links, and the spider, are pivotally coupled to the spool of the driver assembly.

A locking gear 62 of the driver assembly slides freely upon the upstanding shaft 58 of the spool. The long spool pins 61 which extend upwardly from the spool base 57 receive the locking gear 62 and align it with the spool 53. In reviewing FIG. 5 in combination with FIGS. 10 and 11, the locking plate has a pair of internal gear segments 64 which cooperate with gear teeth 65 on the locking gear. The locking plate has a central opening 66 and a pair of wings 67 which have holes 68 therethrough for receiving a pair of locking screws 69. During assembly, the locking plate 63 is mounted onto the locking gear 62 for cooperation therewith and fixed in position when the locking screws 69 are received within a pair of holes 70 (only one hole is shown in FIG. 5) within the nozzle housing 52.

The upstanding shaft 56 of the spool of the driver assembly protrudes from the top of the locking gear 62 to receive a lever block 71. The lever block is prevented from rotating on the upstanding shaft of the spool because a nozzle assembly screw 72 fixes the lever block on the upstanding shaft. Rotation is further prevented due to complementing anti-rotation flats 73 (see also FIG. 14) on the upstanding shaft 56 and lever block 71.

The actuation lever 31 of the driver assembly has a pair of spaced-apart locking cams 74. The locking cams straddle the lever block 71, and a lever pin 75 fixes the actuation lever to the lever block of the driver assembly.

Figure 14:
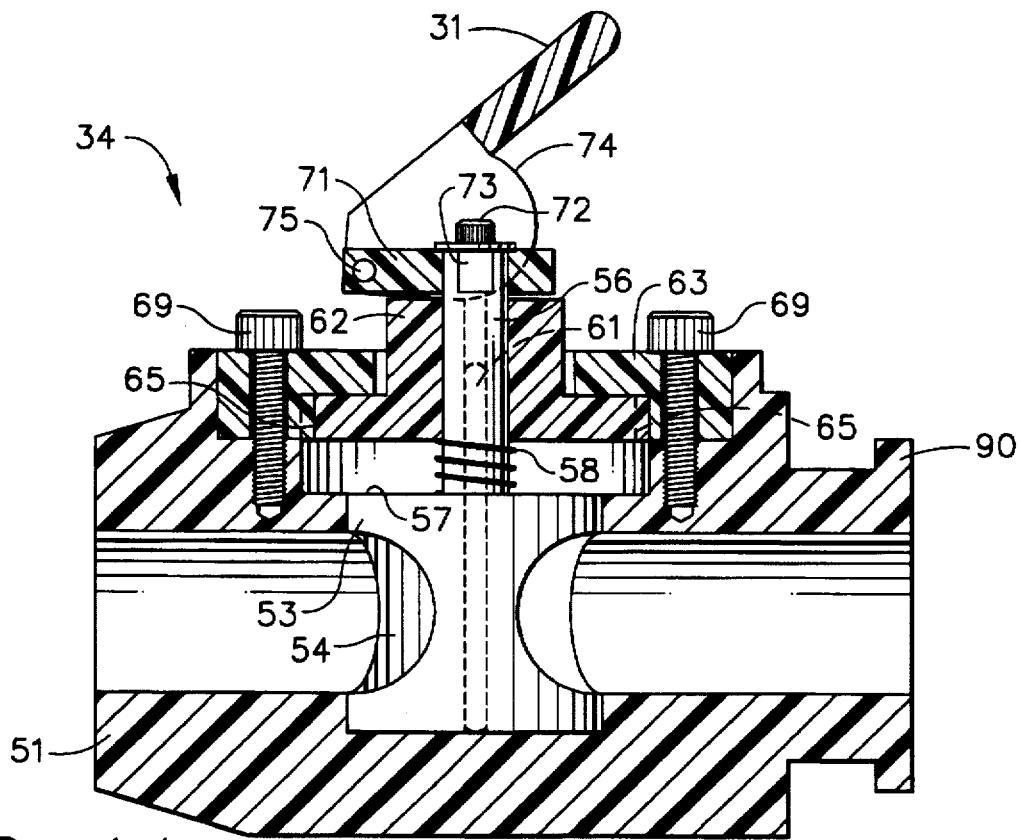
FIG. 14 is a section view of the driver assembly depicted in FIG. 5 shown in its locked position.
Figure 15:
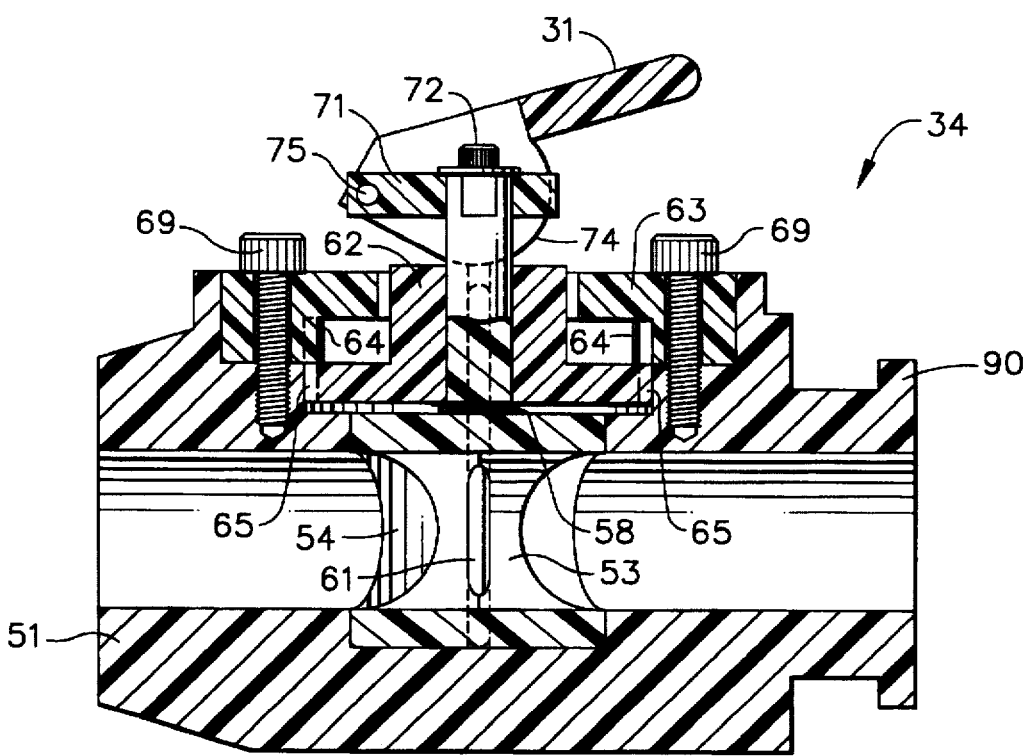
FIG. 15 is a section view of the driver assembly depicted in FIG. 5 shown in its unlocked position.
Figure 16:
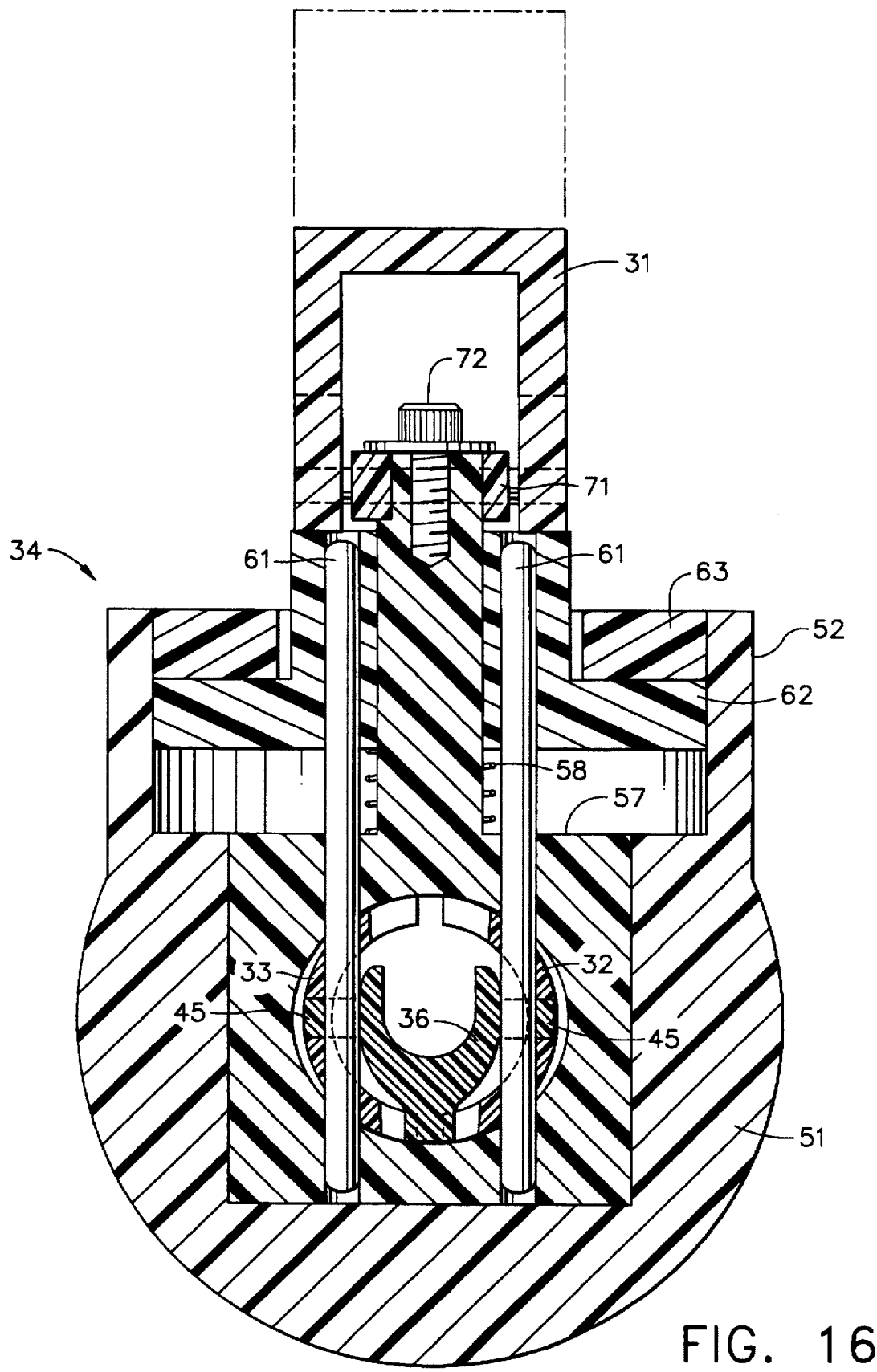
FIG. 16 is a lateral section view of the driver assembly of FIG. 14.

FIGS. 14-16 illustrate the actuation of the driver assembly 34 upon rotational movement of the actuation lever 31. When the driver assembly is in a rest position as illustrated in FIG. 14, the teeth of the locking gear and the teeth of the locking plate are engaged with each other to consequently block the spool in a fixed position. When the actuation lever is depressed, the locking cams 74 of the actuation lever disengage the teeth 65 of the locking gear from the teeth 64 of the locking plate as a downward force is applied against the locking spring 58 mounted on the upstanding shaft 56 of the spool. Consequently, the user can thereafter rotate the actuation lever to correspondingly cause pivotal rotation of the spool within the nozzle housing of the nozzle body from its fixed, rest position to a second rotational position. Release of the actuation lever locks the instrument in the second position by allowing the locking spring 58 to push the locking gear into the locking plate 63. Since the proximal ends of the second and third links are coupled to the spool through the obround hole therein, the pivotal rotation of the spool causes reciprocating longitudinal movement of the second and third links in opposite directions to consequently effect articulation of the end effector.

Figure 17:
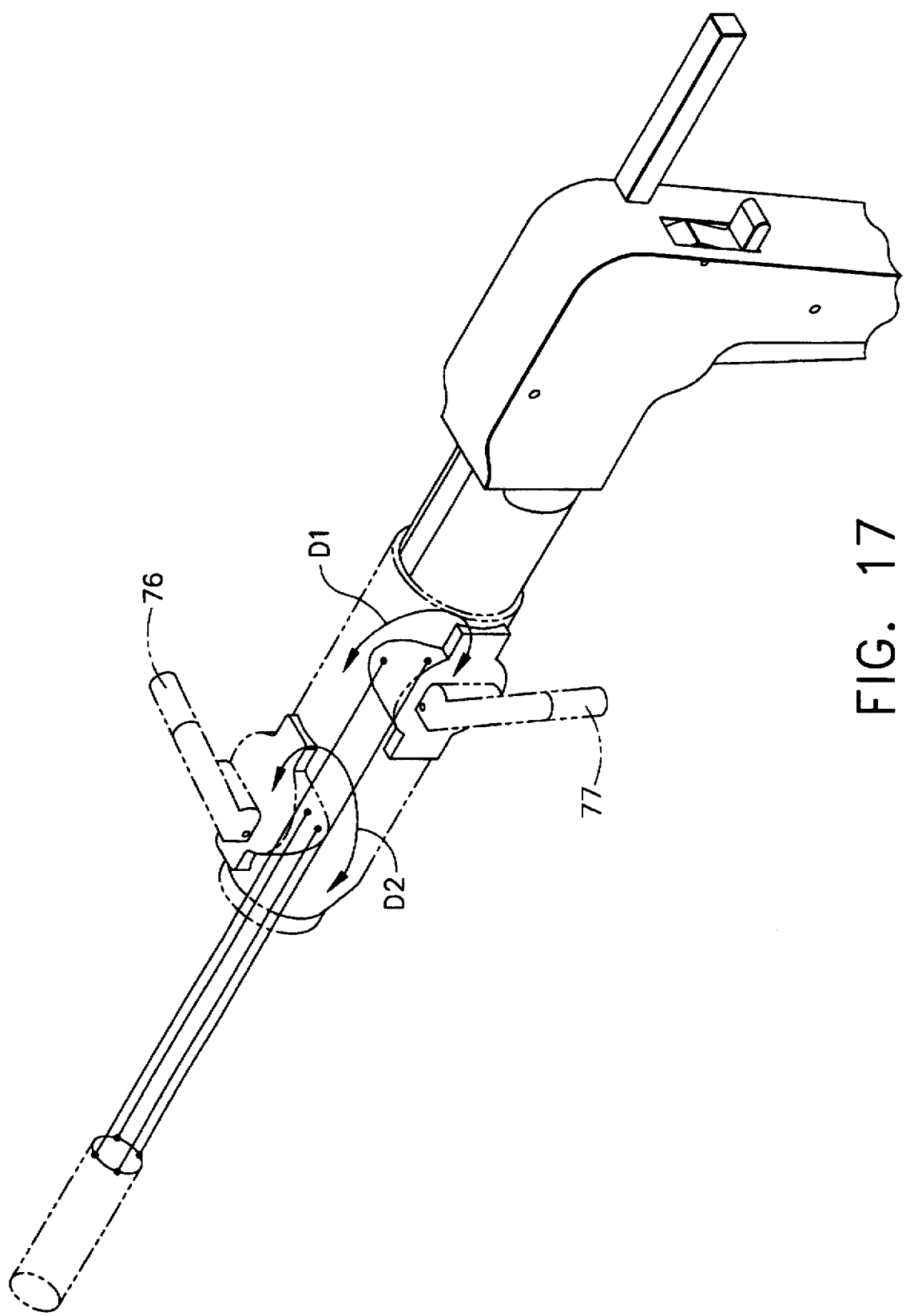
FIG. 17 is a schematic isometric view of an alternate embodiment of a double four bar linkage assembly for an articulating linear stapler.

In the alternate embodiment illustrated in FIG. 17, a double four bar linkage for an endoscopic surgical instrument is illustrated. This linkage includes a horizontal actuating lever 76 and a vertical actuating lever 77. Upon rotational movement of the vertical actuation lever in the direction of the directional arrow designated as "D1", the end effector would articulate in a direction generally perpendicularly to the articulation direction achieved when the horizontal actuating lever is rotated in the manner indicated by the directional arrow designated as "D2". In effect, a dual nozzle and driver assembly is utilized to provide for articulation about planes perpendicular to each other. The vertical actuation lever represents the seventh link, and this seventh link is coupled to fifth and sixth links, which in turn are coupled to the end effector of the instrument. In short, this double four bar linkage can also be viewed as a seven bar linkage.

Figure 18:
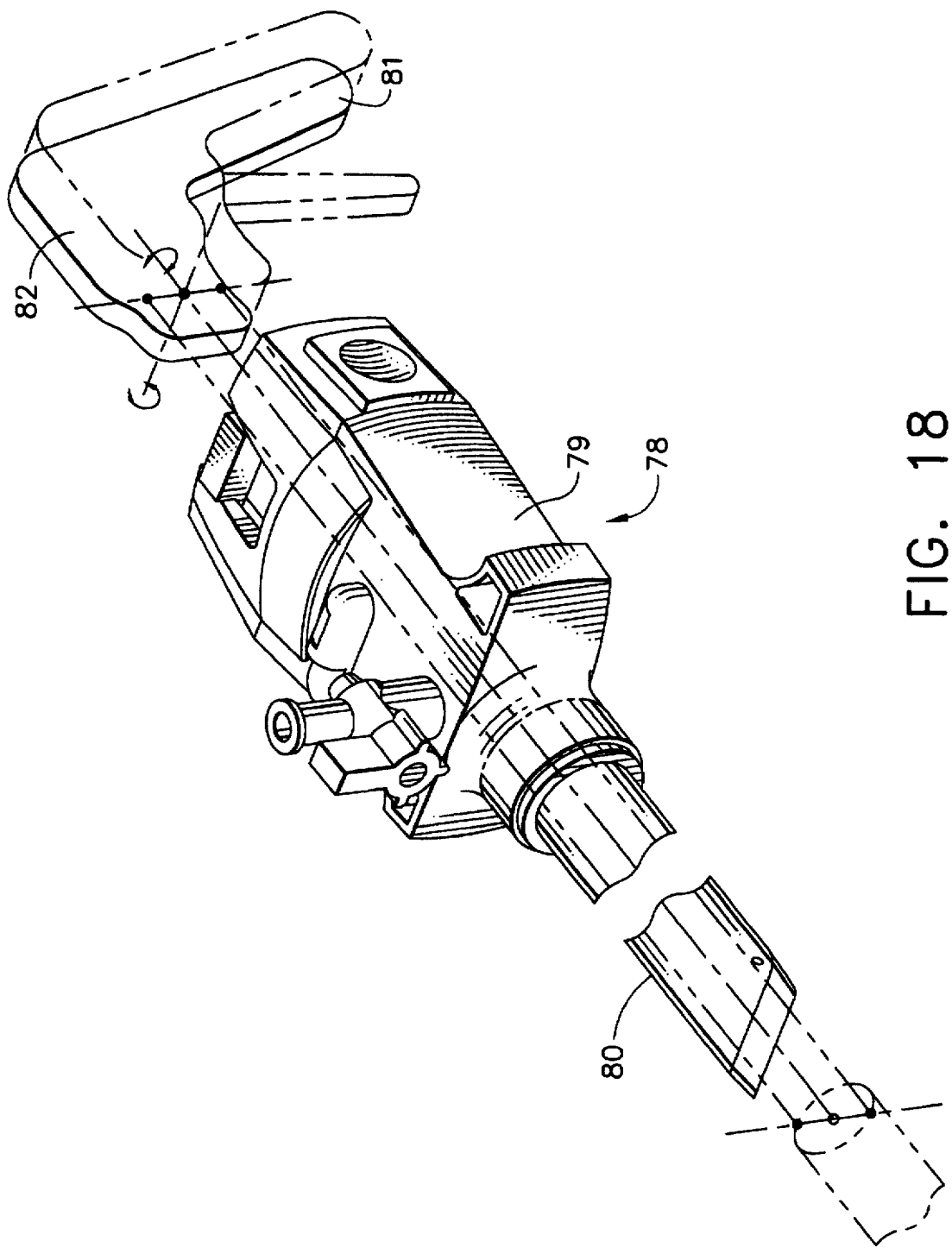
FIG. 18 is a schematic isometric view of yet another alternate embodiment of an articulating linear stapler utilizing a four bar linkage.

In the embodiment illustrated in FIG. 18, a trocar cannula 78 which includes a trocar housing 79 and a cannula sleeve 80 extending therefrom, provides the supporting structure for the second and third links of the four bar linkage of the articulation assembly for the instrument. In this embodiment, the hand grip 81 of the frame 82 of the instrument is rotated in either of the directions indicated by the directional arrows to effect reciprocating movement of the second and third links for corresponding articulation of the end effector.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. An articulation assembly adapted for use with a surgical instrument wherein said instrument has a longitudinal axis, said articulation assembly comprising a four-bar linkage which includes:

a) a first link in the form of an actuation lever operatively connected to said instrument for movement transverse to the longitudinal axis thereof;
  b) second and third links operatively connected to said first link for reciprocating movement by a driver assembly mounted to said instrument, said second and third links being generally parallel to each other and the longitudinal axis, and said second and third links being movable inwardly towards each other from a spaced-apart position to an adjacent position;
  c) a fourth link in the form of an end effector for said instrument attached to said second and third links for movement transverse to the longitudinal axis;

wherein when said first link is pivotally rotated in a first direction from an unactuated position generally parallel to the longitudinal axis to an actuated position:

i) said driver assembly causes said second and third links to move in tandem generally parallel to the longitudinal axis in opposite directions;
  ii) said second and third links move inwardly towards each other from said spaced-apart position to said adjacent position; and
  iii) said fourth link rotates in said first direction from an unarticulated position to an articulated position.

2. The assembly of claim 1 wherein said actuation lever is pivotally connected to said instrument for movement transverse to the longitudinal axis thereof.

3. The assembly of claim 2 wherein each of said second and third links is an elongated, rigid link having an arcuate concave surface thereon, and the arcuate concave surface of said second link faces the arcuate concave surface of said third link.

4. The assembly of claim 3 further comprising a pivot block coupled to a proximal end of said fourth link, wherein a distal end of each said second and third links is pivotally attached to said pivot block.

5. The assembly of claim 4 wherein said driver assembly includes a nozzle body mounted to said instrument having a nozzle housing extending therefrom, and a spool received within said nozzle housing of said nozzle body, said spool being operatively coupled to said first link for rotational movement within said nozzle housing in response to pivotal movement of said first link, wherein a proximal end of each of said second and third links is attached to said spool and rotational movement of said spool causes a corresponding reciprocating movement of said second and third links.

6. The assembly of claim 5 further comprising an elongated, lateral support spider interposed between, and coupled to, said second and third links.

7. The assembly of claim 6 wherein said lateral support spider has a central channel therethrough.

8. The assembly of claim 7 further comprising fifth and sixth links operatively connected at proximal ends thereof to a seventh link in a form of a second actuation lever pivotally mounted on said instrument and at distal ends thereof to said fourth link, wherein when said seventh link is pivotally rotated, said fifth and sixth links cause said first link to rotate in a third direction generally perpendicular to said second direction.

* * * * *